May 30, 1972 M. S. TRINTA Plant Pat. 3,201
ALMOND TREE
Filed Jan. 8, 1971
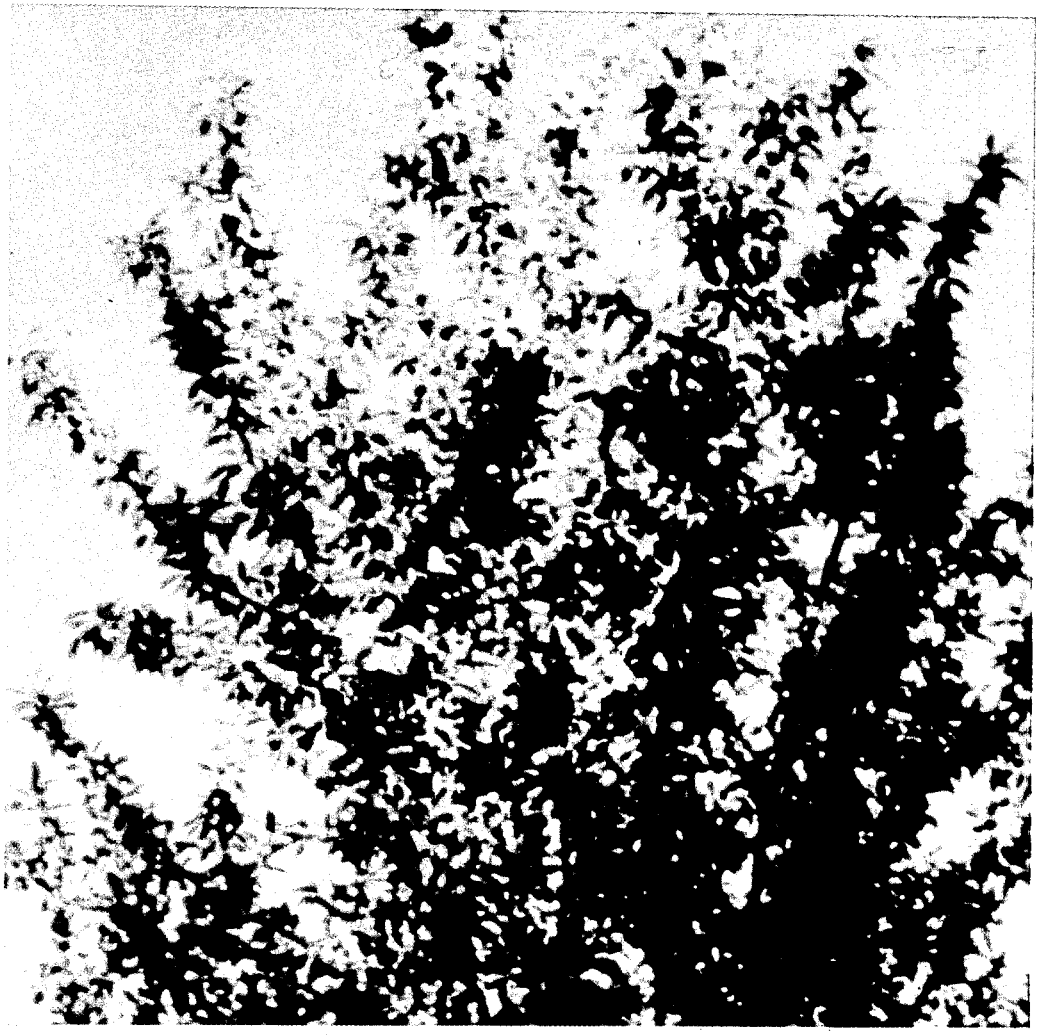
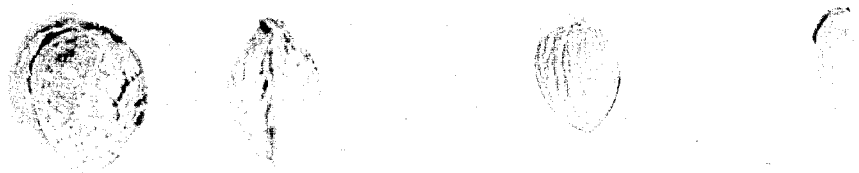
INVENTOR
Manuel S. Trinta
BY
Webster & Webster
ATTORNEYS United States Patent Office Plant Pat. 3,201
Patented May 30, 1972

3,201
ALMOND TREE

Manuel S. Trinta, 706 Pomelo Ave.,
Patterson, Calif. 95363
Filed Jan. 8, 1971, Ser. No. 105,136
Int. Cl. A01h 5/03
U.S. Cl. Plt.—30 1 Claim

ABSTRACT OF THE DISCLOSURE

An almond tree, of medium size, which is vigorous, dense when young but more open when mature, upright to spreading, abundant of foliage with medium size leaves, and a regular and heavy producer of nuts well distributed on the tree; the nuts, which harvest easily and relatively early, being small, of very good quality, and averaging, by weight, forty-five to fifty percent kernel to nut, and with about forty kernels per ounce.

*Origin of the variety*

The present variety of almond tree was discovered by me growing, as a seedling, alongside a Mission (unpatented) almond tree in an orchard on my ranch located near Patterson, Stanislaus County, Calif. As such seedling, upon continued observation, evidenced certain novel and desirable characteristics, I asexually reproduced it in anticipation of subsequent growing as a commercial variety.

*Asexual reproduction of the variety*

I asexually reproduced the present variety of almond tree—on my ranch located as aforesaid—by grafting the same onto seedlings of almond root, and, in maturity, such reproductions ran true to the original tree in all respects.

*Summary of the variety*

The present variety of almond tree is of medium size, vigorous, dense when young but more open when mature, upright to spreading, abundant of foliage with medium size leaves, and a regular and heavy producer of small, very good quality, nuts well distributed on the tree and remaining thereon until ready to harvest the entire tree and which is accomplished early and with one knocking. Such harvest is about three to five days before the Nonpareil (unpatented), and, in comparison to the latter, the nuts are smaller; the small, uniform, sweet, light color kernels being most desirable for confection manufacture.

Further, the small nuts of the present variety of almond tree average, by weight, forty-five to fifty percent kernel to nut, and with about forty kernels per ounce.

Additionally, the nuts of the present variety of almond tree are well sealed; this being an advantage in that insect infestation is minimized, and the nuts are more adaptable to mechanical harvesting.

*Brief description of the drawing*

The drawing is an illustration, by photographic reproduction in color, of a portion of the present almond tree in bearing, and, separately shown, nuts out of hull, and meats out of shell.

*Description of the variety*

The botanical details of this new and distinct variety of almond tree—with color definitions in common terms—are as follows:

Tree:
- *Density.*—Dense when young; more open when mature.

- *Size.*—Medium.
- *Vigor.*—Vigorous.

Trunk:
- *Form.*—Medium.
- *Texture.*—Medium.

Branches:
- *Form.*—Medium.
- *Texture.*—Medium.
- *Lenticels.*—Medium number; small size.
- *Branching habit.*—Upright to spreading.
- *Color.*—New wood—brown, dull; mature wood—gray, dull.

Foliage: Quantity.—Abundant.

Leaves:
- *Size.*—Medium; average length—3⅛"; average width—⅞".
- *Shape.*—Lanceolate; acutely pointed.
- *Thickness.*—Medium.
- *Texture.*—Smooth.
- *Margin.*—Crenate; finely serrate.
- *Petiole.*—Long; slender.
- *Glands.*—Average number—2; opposite; small; globose; green; usually positioned immediately adjacent base of blade.
- *Stipules.*—Very small
- *Color.*—Top side—dark green, glossy. Under side—dark green, semi-dull.

Bloom:
- *Amount of bloom.*—average.
- *Color.*—Very light pink, changing to white as bloom progresses.
- *Blooming period.*—Average date: First bloom—February 3rd; ¾ bloom—February 15th; blooms with Nonpareil.

Crop:
- *Bearing.*—Regular bearer.
- *Productivity.*—Heavy.
- *Distribution of nuts on tree.*—Well distributed.
- *Harvest period.*—Average date—August 1st; early—about 3 to 5 days before Nonpareil.
- *Tenacity.*—Hangs well on tree; easy to harvest, with one knocking; easy to hull.

Hull:
- *Outer surface.*—Smooth.
- *Pits.*—Slightly pitted.
- *Form.*—Regular.
- *Thickness.*—Thin.
- *Flesh.*—Fleshy.
- *Suture.*—Ridged.
- *Color.*—Medium green.
- *Dehiscence.*—Opens freely.
- *Splitting.*—Along suture.

Nut:
- *Size.*—Small; average length—⅞"; average width—⅝"; average thickness—½"; average weight—20 per ounce.
- *Form.*—Length/width — ovate.Width/thickness — medium.
- *Shell.*—Paper; soft; thin; smooth. Outer shell—crumbling; adheres to hull. Inner shell—hard; well sealed.
- *Color.*—Medium light.
- *Pits.*—Small; numerous; shallow; irregular.
- *Base.*—Venturally oblique.
- *Stem scar.*—Small; obtuse.
- *Apex.*—Obtuse; blunt.
- *Wing.*—Broad; thick; tapered toward apex.
- *Inner surface.*—Medium.

*Ventral streak.*—Medium color; board; short; point obtuse

*Percentage of kernel to nut.*—45–50%.

Kernel:

*Size.*—Small; uniform; average length—11/16"; average width—½"; average thickness—5/16"; average weight—40 kernels per ounce.

*Form.*—Length/width — ovate. Width/thickness — medium.

*Base.*—Ventrally oblique.

*Stem scar.*—Small obtuse.

*Apex.*—Obtuse blunt.

*Texture.*—Wrinkled.

*Pellicle.*—Thin.

*Pubescence.*—Smooth.

*Color.*—Light brown.

*Number of doubles.*—Few.

*Defective kerenls.*—Gummy—none; corky—none; deformed—none; blanks—few.

*Flavor.*—Sweet; normal; good.

*Quality.*—Very good.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, which is of medium size, vigorous, dense when young but more open when mature, upright to spreading, abundant of foliage with medium size leaves, and a regular and heavy producer of small, very good quality, nuts well distributed on the tree and remaining thereon until ready to harvest the entire tree and which is accomplished early and with one knocking; the harvest being about three to five days before the Nonpareil, and the nuts—which are well sealed—being smaller; and the kernels being uniform, sweet, light in color, and small, averaging—by weight—forty-five to fifty percent kernel to nut, with about forty kernels to the ounce.

No references cited.

ROBERT E. BAGWILL, Primary Examiner